(12) United States Patent
Chilakala et al.

(10) Patent No.: US 11,541,066 B2
(45) Date of Patent: Jan. 3, 2023

(54) STABLE READY-TO-USE PARENTERAL COMPOSITIONS OF FOSAPREPITANT

(71) Applicant: EXTROVIS AG, Baar (CH)

(72) Inventors: Krishna Mohan Chilakala, Hyderabad (IN); Hanumantha Rao Kamma, Baar (CH); Janos Vaczi, Kuessnacht am Rigi (CH)

(73) Assignee: EXTROVIS AG, Baar (CH)

( * ) Notice: Subject to any disclaimer, the term of this patent is extended or adjusted under 35 U.S.C. 154(b) by 0 days.

(21) Appl. No.: 17/685,636

(22) Filed: Mar. 3, 2022

(65) Prior Publication Data

US 2022/0280539 A1 Sep. 8, 2022

(30) Foreign Application Priority Data

Mar. 4, 2021 (IN) ............................. 202121009070
Aug. 25, 2021 (IN) ............................. 202121038428

(51) Int. Cl.
*A61K 31/675* (2006.01)
*A61K 9/00* (2006.01)

(52) U.S. Cl.
CPC .......... *A61K 31/675* (2013.01); *A61K 9/0019* (2013.01)

(58) Field of Classification Search
CPC ................................................... A61K 31/675
See application file for complete search history.

(56) References Cited

U.S. PATENT DOCUMENTS

| | | |
|---|---|---|
| 5,691,336 A | 11/1997 | Dorn et al. |
| 5,716,942 A | 2/1998 | Dorn et al. |
| 9,913,853 B2 * | 3/2018 | Malhotra ............. A61K 9/0019 |
| 10,307,432 B2 | 6/2019 | Malhotra et al. |
| 2018/0235973 A1 * | 8/2018 | Chandrashekhar .... A61K 47/40 |
| 2019/0350947 A1 | 11/2019 | Yu et al. |
| 2019/0358249 A1 | 11/2019 | Patel |
| 2020/0237788 A1 | 7/2020 | Patel |

FOREIGN PATENT DOCUMENTS

| | | |
|---|---|---|
| CN | 103156813 A | 6/2013 |
| CN | 104042572 B | 4/2016 |

* cited by examiner

*Primary Examiner* — Rei Tsang Shiao
(74) *Attorney, Agent, or Firm* — Medler Ferro Woodhouse & Mills PLLC

(57) ABSTRACT

The present invention provides stable ready-to-use parenteral compositions of fosaprepitant and its pharmaceutically acceptable salts or derivatives. The compositions of the present invention do not require reconstitution and/or dilution prior to administration to the patient, and are stable over the shelf-life of the product.

8 Claims, No Drawings

STABLE READY-TO-USE PARENTERAL COMPOSITIONS OF FOSAPREPITANT

FIELD OF THE INVENTION

The present invention provides stable ready-to-use parenteral compositions of fosaprepitant and its pharmaceutically acceptable salts or derivatives. The compositions of the present invention do not require reconstitution and/or dilution prior to administration to the patient, and are stable over the shelf-life of the product.

BACKGROUND

Fosaprepitant, a substance P/neurokinin-1 (NK1) receptor antagonist, is an antiemetic agent, typically used as its dimeglumine salt, and is chemically described as 1-Deoxy-1-(methylamino)-D-glucitol[3-[[(2R,3S)-2-[(1R)-1-[3,5-bis(trifluoromethyl)phenyl]ethoxy]-3-(4-fluorophenyl)-4-morpholinyl]methyl]-2,5-dihydro-5-oxo-1H-1,2,4-triazol-1-yl] phosphonate. The structure of fosaprepitant dimeglumine is as follows—

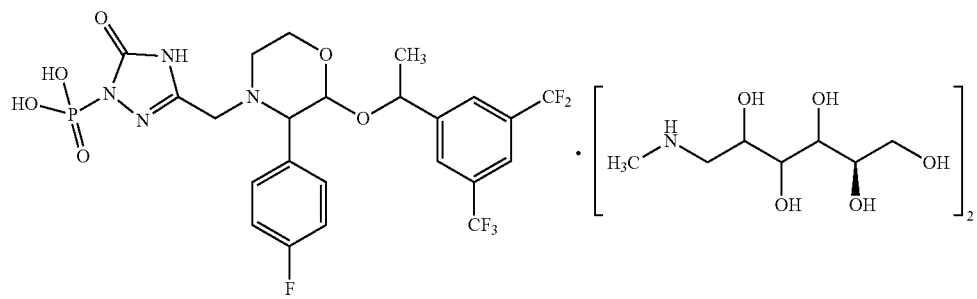

Formula I

U.S. Pat. No. 5,691,336 to Dorn et al, discloses the compound Fosaprepitant and further describes methods of synthesizing the said compound. U.S. Pat. No. 5,716,942, also to Dorn et al, discloses the use of neurokinin-1 receptor antagonists, such as Fosaprepitant, for the treatment of inflammatory diseases, pain or migraine, asthma, emesis and nausea.

It was first approved as Emend® from Merck in the form of an injection, for use in combination with other antiemetic agents. It is indicated in adults and pediatric patients 6 months of age and older for the prevention of—(1) acute and delayed nausea and vomiting associated with initial and repeat courses of highly emetogenic cancer chemotherapy (HEC) including high-dose cisplatin, and (2) delayed nausea and vomiting associated with initial and repeat courses of moderately emetogenic cancer chemotherapy (MEC). Commercially, EMEND® injection is available as a white to off-white lyophilized powder in single-dose glass vial for reconstitution. The lyophilized cake containing fosaprepitant dimeglumine (equivalent to 150 mg of fosaprepitant) is first reconstituted with 5 ml of 0.9% Sodium Chloride Injection, USP and the vial is shaken to dissolve the cake. The entire 5 ml of solution thus obtained is withdrawn and aseptically added to 145 ml of 0.9% Sodium Chloride Injection, USP in an infusion bag, to yield a total volume of 150 ml and a concentration on 1 mg/ml of fosaprepitant. In pediatric patients, a lower dose and therefore a smaller volume of the reconstituted solution would be required. Emend® for injection is incompatible with any solutions containing divalent cations (e.g., $Ca^{2+}$, $Mg^{2+}$), including Lactated Ringer's Solution and Hartmann's Solution. The reconstituted final drug solution is stable for only 24 hours at ambient room temperature [at or below 25° C. (77° F.)].

There are several areas of concern for such a presentation that requires reconstitution, followed by dilution. The reconstitution needs to be conducted in an aseptic manner, and could possibly lead to contamination of the product, if not done correctly. There is also the possibility of under or over-dosing of the drug, if the wrong amount is withdrawn from the reconstituted vial and added to the diluent in the infusion bag. Similarly, use of incompatible diluent(s) could lead to other issues of physical and/or chemical stability. Further, the commercially available composition is stable for only 24 hours subsequent to reconstitution and dilution, which could lead to significant wastage of the product.

United States Patent Application No 20180235973 (the '973 publication), titled "Liquid formulations of fosaprepitant", purports to provide solutions of fosaprepitant that are ready to dilute, i.e. a preconcentrate, and solutions that are ready to administer. However, the specification and working examples of the application only provide details on preconcentrate solutions of fosaprepitant having a volume of 1 ml, 2 ml or 2.6 ml. There is no teaching in the application about solutions that are ready to administer, i.e. solutions having a volume of 150 ml and containing 150 mg of fosaprepitant. Equally absent from the disclosure of this application are directions on obtaining such solutions and stabilizing them over a longer period of time, such as over the shelf-life.

Fosaprepitant dimeglumine easily degrades to Aprepitant, unless stored at low temperature. Therefore, it is conventionally supplied as a lyophilized formulation to reduce the formation of impurities and to improve the stability of the final formulation. The lyophilized vials are to be stored at a temperature of about 2 to about 8 degrees Celsius. As mentioned above, upon reconstitution, the solution is stable for a maximum of 24 hours at ambient room temperature, and any remaining solution is discarded after 24 hours. Some of the problems faced by Emend® injection product are the possible contamination during reconstitution and dilution, under or over dosing, and use of wrong diluents.

SUMMARY OF THE INVENTION

The present invention provides a stable injectable pharmaceutical composition comprising fosaprepitant or its pharmaceutically acceptable salt or solvate; at least one pharmaceutically acceptable solvent; at least one pharmaceutically acceptable isotonic agent; optionally at least one pharmaceutically acceptable solubilizing agent and optionally at least one pharmaceutically acceptable stabilizing agent, wherein the composition is ready-to-use.

The present invention provides a stable injectable pharmaceutical composition comprising fosaprepitant or its pharmaceutically acceptable salt or solvate; at least one pharmaceutically acceptable solvent; at least one pharmaceutically acceptable stabilizing agent, wherein the composition is ready-to-use.

In a preferred embodiment, the ready-to-use composition of the present invention containing fosaprepitant comprises a solvent selected from the group consisting of water for injection, ethanol, propylene glycol, polyethylene glycol, propanol, and mixtures thereof.

In another preferred embodiment, the ready-to-use composition of the present invention containing fosaprepitant contains one or more pharmaceutically acceptable stabilizing agents.

In a preferred embodiment, the ready-to-use composition of the present invention containing fosaprepitant comprises a stabilizing agent selected from the group consisting of (i) a chelating agent selected from disodium EDTA and calcium disodium EDTA, (ii) an amino acid selected from the group consisting of glycine, 1-arginine, phenylalanine, histidine, acetylcysteine, citrulline, lysine, and isoleucine, methionine, cysteine and their pharmaceutically acceptable salts, and (iii) a combination thereof.

In another preferred embodiment, the ready-to-use composition of the present invention containing fosaprepitant has a pH of about 6.5 to about 10.0.

DESCRIPTION

A study of prior art reveals that attempts have been made to solve the above described problems but none has led to a large volume infusion dosage form of fosaprepitant, wherein the dosage form is a stable solution of fosaprepitant or its pharmaceutically acceptable salt, in an aqueous vehicle, in a large volume infusion container. The present invention provides a stable, ready-to-use infusion of fosaprepitant which contains 150 ml of a sterile solution of fosaprepitant dimeglumine in an infusion bag, and which is stable over its shelf-life. The composition of the present invention overcomes the problems faced by the prior art Emend® injection, and is also advantageous over the prior art '973 publication, in that the composition of the invention is stable over extended periods of time in the liquid state, without having to undergo a step of dilution. The ready-to-use composition of the present invention avoids the inconvenience of reconstituting and diluting a concentrated small volume parenteral formulation with infusion diluents prior to infusion, as well as eliminates the risk of microbiological contamination during aseptic handling and any potential calculation or dilution error that could lead to under or over dosing. Thus, it provides a substantial advancement over the art, and a major convenience to patients and care-givers.

The ready-to-use composition of the present invention is a "stable" and "ready to be infused" fosaprepitant composition, meaning that the composition is stable over time, is sterile, has a volume in excess of 100 ml and can be directly infused intravenously, without any intervening step of reconstitution or dilution or mixing.

The term 'stable', as used in the context of this application, means remaining in a state or condition that is suitable for administration to a patient. In particular, a "stable composition" is intended to refer to a composition which when stored at about 2° C. to about 8° C., for a defined period of time, is physically stable, i.e. no appearance of visible particulates, and is also chemically stable, i.e. the chemical impurities are within a narrow acceptable range. Particularly, the term "chemically stable" as used herein means that when the composition is stored at about 2° C. to about 8° C., the impurities such as those resulting from chemical reaction in solution, remain within acceptable limits over a long period of time. It is intended that the period of time over which the composition is stable for, is 7 days, 1 month, 2 months, 3 months, 4 months, 5 months, 6 months, 7 months. 8 months, 9 months, 10 months, 11 months, 12 months, 13 months, 14 months, 15 months, 16 months, 17 months, 18 months. 19 months, 20 months, 21 months, 22 months, 23 months or 24 months.

In one embodiment, at least about 90% purity of the fosaprepitant is retained after storage at 2-8° C. More preferably, at least about 92% purity of the fosaprepitant is retained after storage at 2-8° C. More preferably, at least about 95% purity of the fosaprepitant is retained after storage at 2-8° C. Still more preferably, at least about 96% purity of the fosaprepitant is retained after storage at 2-8° C. Most preferably, at least about 98% purity of the fosaprepitant is retained after storage at 2-8° C.

In another aspect of the present invention, the ready to use compositions of fosaprepitant are described. These compositions comprise fosaprepitant, one or more inert excipients selected from diluents, solvents, cosolvents, isotonicity agents, chelating agents, buffers, pH-adjusting agents, solubilizers, stabilizers, and the like. In preferred embodiments the composition has a concentration of fosaprepitant of about 0.5 mg/ml to about 10 mg/ml. In preferred embodiments the composition has a concentration of fosaprepitant of about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml. In highly preferred embodiments, the composition has a concentration of fosaprepitant of about 1 mg/ml.

In one embodiment, the diluent used in the composition of the present invention may be selected from lactose, mannitol, sucrose, trehalose, dextran, hydroxyethyl starch, ficoll and gelatin.

In one embodiment the composition has a concentration of diluent of about 0.1 mg/ml to about 10 mg/ml. In preferred embodiment the composition has a concentration of diluent of about 1 mg/ml, about 2 mg/ml, about 2.5 mg/ml, about 3 mg/ml, about 3.5 mg/ml, about 4 mg/ml, about 4.5 mg/ml, about 5 mg/ml, about 5.5 mg/ml, about 6 mg/ml, about 6.5 mg/ml about 7 mg/ml, about 7.5 mg/ml, about 8 mg/ml, about 8.5 mg/ml, about 9 mg/ml, about 9.5 mg/ml, about 10 mg/ml. In preferred embodiment the composition has a concentration of diluent of about 2.5 mg/ml.

In one embodiment, the solvent used in the composition of the present invention may be selected from, but is not limited to, the group comprising water for injection, propylene glycol, polyethylene glycol, propanol, dimethyl acetamide, solketal, glycerol formal, glycerol, glycofurol, diethylene glycol monoethyl ether, dimethyl sulfoxide, N-methyl-2-pyrrolidone, dimethyl formamide and mixtures thereof. In a highly preferred embodiment of the present invention, the solvent used is water for injection. The solvent helps to dissolve the fosaprepitant, thereby providing compositions of fosaprepitant that are physically and chemically stable over a long period of time.

In another embodiment the composition can optionally contain a solubilizing agent, such as docusate sodium, glyceryl monooleate, polyoxyl-35-castor oil (also known as PEG-35 castor oil or Cremophor EL or macrogolglycerol ricinoleate), sodium lauryl sulfate, or sorbitan esters. The solubilizing agent or surfactant may optionally be a polyoxyethylenesorbitan fatty acid ester. Polyoxyethylenesorbitan fatty acid esters are also referred to as polysorbates, e.g., polysorbate 80 (polyoxyethylene sorbitan monooleate, Tween 80), polysorbate 40 and polysorbate 20.

In one embodiment the composition has a concentration of solubilizing agent of about 0.01 mg/ml to about 5 mg/ml. In another preferred embodiment the composition has a concentration of solubilizing agent of about 0.1 mg/ml to about 5 mg/ml. In another preferred embodiments, the concentration of solubilizing agent in the composition is about 0.1 mg/ml, about 0.2 mg/ml, about 0.3 mg/ml, about 0.4 mg/ml, about 0.5 mg/ml, about 0.6 mg/ml, about 0.7 mg/ml, about 0.8 mg/ml, about 0.9 mg/ml, about 1 mg/ml, about 2 mg/ml, about 3 mg/ml, about 4 mg/ml or about 5 mg/ml. In highly preferred embodiments the composition has a concentration of solubilizing agent of about 0.5 mg/ml.

In another embodiment, the ready to use composition contains one or more stabilizing agents. The stabilizing agent may be selected from, but is not limited to, (i) a chelating agent selected from disodium EDTA and calcium disodium EDTA, (ii) an amino acid selected from the group consisting of glycine, 1-arginine, phenylalanine, histidine, acetylcysteine, citrulline, lysine, isoleucine, methionine, cysteine and their pharmaceutically acceptable salts, or (iii) a combination thereof.

In one embodiment, the stabilizing agent is L-Arginine. In another embodiment, the stabilizing agent is glycine. In yet another embodiment, the stabilizing agent is phenylalanine. In yet another embodiment, the stabilizing agent is disodium EDTA.

In still another embodiment, the stabilizing agent is histidine. In a preferred embodiment, the stabilizing agent is a mixture of arginine and disodium EDTA.

In preferred embodiments, the amount of stabilizing agent in the composition is about 0.01 mg/ml, about 0.02 mg/ml, about 0.03 mg/ml, about 0.04 mg/ml, about 0.05 mg/ml, about 0.06 mg/ml, about 0.07 mg/ml, about 0.08 mg/ml, about 0.09 mg/ml, about 0.1 mg/ml, about 0.2 mg/ml, about 0.3 mg/ml, about 0.4 mg/ml, about 0.5 mg/ml.

Another embodiment of the invention optionally contains one or more pH adjusting agents, the one or more pH adjusting agent being selected from sodium hydroxide, calcium hydroxide, potassium hydroxide, sodium bicarbonate, sodium carbonate, sodium carbonate decahydrate, sodium carbonate monohydrate, diethanolamine, meglumine, tromethamine, ammonia, hydrochloric acid, acetic acid, acetic anhydride, adipic acid, anhydrous citric acid, amino acids such as glycine, 1-arginine, phenylalanine, histidine, acetylcysteine, citrulline, lysine, isoleucine, methionine, cysteine, and mixtures thereof.

The pH of the composition of the present invention ranges from about 6.5 to about 10.0. The pH is adjusted such that the composition is stable over its entire manufacturing process and through its shelf-life.

Another embodiment of the present invention optionally contains one or more isotonic agents. Preferably, the isotonic agent is selected from, but is not limited to, the group comprising polyethylene glycol, glycerol, sodium chloride, glucose and mixtures thereof. Typically, the isotonic agent is used in an amount sufficient to provide an osmolality in the range of about 100 mOsMol/Kg to about 500 mOsMol/Kg, more preferably about 150 mOsMol/Kg to about 400 mOsMol/Kg, still more preferably about 280 mOsMol/Kg to about 320 mOsMol/Kg, and most preferably about 300 mOsMol/Kg. In highly preferred embodiments, the isotonic agent is sodium chloride and is present in an amount of about 5 mg/ml to about 10 mg/ml, more preferably about 7.5 mg/ml, and most preferably about 8 mg/ml.

A pharmaceutically acceptable parenteral composition is also provided comprising fosaprepitant and an aqueous solvent, such as water for injection or saline, wherein the composition includes:

about 0.0001-0.005% w/v disodium edetate;

about 0.1-5.5% w/v of a diluent, such as lactose monohydrate;

about 0.01-5.0% w/v of a stabilizing agent, such as L-arginine;

about 0.01-1% w/v of a isotonic agent, such as sodium chloride; and about 0.01-5.0% w/v of a solubilizing agent, such as polysorbate 80.

In yet another embodiment, a pharmaceutically acceptable parenteral composition comprises fosaprepitant and an aqueous solvent, such as water for injection, wherein the composition includes:

about 0.0001-0.005% w/v disodium edetate;

about 0.1-5.5% w/v of a diluent, such as lactose monohydrate;

about 0.01-5.0% w/v of a solubilizing agent, such as polysorbate 80.

about 0.01-5% w/v of a isotonic agent, such as sodium chloride; and pH adjusting agents such as sodium bicarbonate and/or sodium carbonate.

The ready-to-use fosaprepitant parenteral composition of the present invention is packaged in a polymeric single-compartment container that is compatible with the composition. Suitable polymeric single-compartment containers include, for example, glass or polymeric vials, infusion bags or infusion bottles with sizes ranging from about 100 ml to about 250 ml. These large volume parenteral presentations can be contained in infusion bags or bottles preferably purged with nitrogen, Single-compartment polymeric containers are preferably flexible and can contain, or may be free of, polyvinylchloride (PVC). In one of the embodiments, the ready-to-use composition contains 150 ml of the stable composition of fosaprepitant dimeglumine in an aqueous vehicle, packaged in a single-compartment infusion bag made of polypropylene. Other alternative packaging systems suitable for providing the stable ready-to-use composition of the present invention may have the material of construction of the infusion container made of multilayer M312 with one tube polyolefins/EVA. Other suitable packaging systems include infusion bags made of high barrier film that is impermeable to gas and water. The infusion containers include an injection port made of medical-grade polycarbonate, which can be sterilized. It allows for drug supplementation and its internal membrane is latex-free. Preferably, the infusion bags and injection port are made of materials that are free of plasticizers.

As discussed above, the fosaprepitant ready-to-use composition of the present invention is stable over its shelf life, when stored at refrigerated conditions, i.e. from about 2° C. to about 8° C. The specification for impurities in the ready-to-use composition, at shelf-life is as seen in Table 1 below—

TABLE 1

Impurity specification at shelf-life for ready-to use compositions of the present invention

| Impurity | Specification |
| --- | --- |
| Impurity C (Aprepitant) | Not more than 5% |
| Impurity F | Not more than 0.20% |
| Maximum Unknown Impurity | Not more than 0.20% |
| Total Impurities | Not more than 6% |

The impurities are described below.

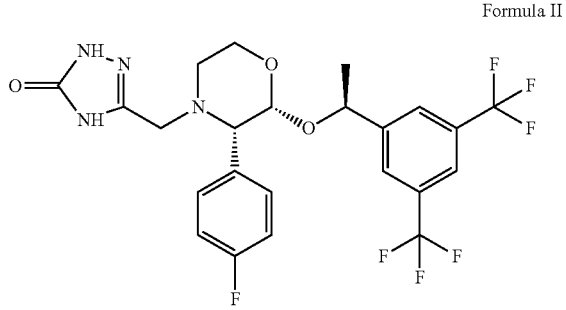 [SMILES: C[C@H](O[C@H]1OCCN(Cc2n[nH]c(=O)[nH]2)[C@H]1c1ccc(F)cc1)c1cc(C(F)(F)F)cc(C(F)(F)F)c1]

Formula II

Impurity C, compound of formula II, is chemically known as 5-[[2(R)-[1(S)-[3,5-bis(trifluoromethyl)phenyl]ethoxy]-3(S)-(4-fluorophenyl)-4-morpholinyl]methyl]-1,2-dihydro-3H-1,2,4-triazol-3-one, also known as Aprepitant.

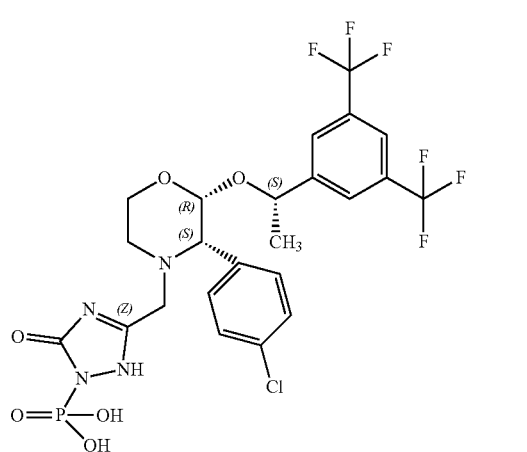

Formula III

Impurity F, compound of formula III, is chemically known as (3-(((2R,3S)-2-((S)-1-{3,5-bis(trifluoromethyl)phenyl)ethoxy)-3-(4-chlorophenyl)morpholino) methyl)-5-oxo-2,5-dihydro-1H-1,2,4-triazol-1-yl) phosphoric acid.

EXAMPLES

Example 1

A fosaprepitant ready-to-use solution for infusion was prepared as detailed below.

| Ingredients | Quantity (mg/mL) | Quantity Per bag (150 mL) |
| --- | --- | --- |
| Fosaprepitant Dimeglumine | 1.635 | 247.5 mg |
| Disodium EDTA | 0.036 | 5.4 mg |
| Lactose monohydrate | 2.50 | 375 mg |
| Polysorbate - 80 | 0.50 | 75 mg |
| Sodium bicarbonate | 1.33 | 199.5 mg |
| Sodium carbonate | 0.16 | 24 mg |
| Sodium Chloride | 9.00 | 1350 mg |
| Sterile water for injection | | QS to 150 mL |

80% of batch quantity of sterile water for injection was taken, and batch quantity of sodium chloride was added to the above solution under continuous stirring. Batch quantity of Sodium bicarbonate was then added to the above solution under continuous stirring. This was followed by addition of batch quantity of Sodium carbonate under stirring. Disodium EDTA was added with stirring. Lactose monohydrate was then added to the solution under stirring, followed by addition of Polysorbate 80. The solution so obtained was cooled to 2-8° C., and the pH was found to be around pH 8.42. The fosaprepitant dimeglumine was then added to the solution under stirring. The volume of the solution was made up to 150 mL with sterile water for injection. The final pH of the solution was 8.73. This bulk solution was filtered under pressure using PVDF 0.22 µm capsule filter. 150 ml of the filtered solution was aseptically filled into infusion bags made of polypropylene, free of any plasticizer and stored at 2-8° C.

Example 2

The fosaprepitant solution obtained in Example 1, packaged in infusion bags, and stored at 2-8° C. was subjected to testing. The results of the real time testing are included in Table 2 below. Table 2 also provides the preferred specifications for the compositions of the present invention.

TABLE 2

| | Specification | Initial | 2 M | 3 M |
| --- | --- | --- | --- | --- |
| Description | Clear colorless solution | Clear colorless solution | Clear colorless solution | Clear colorless solution |
| pH | 6.5-10.0 | 8.68 | 8.86 | 8.93 |
| Assay of Fosaprepitant | 90-110% | 98.9 | 100.9 | 98.7 |
| Related Substances | | | | |
| Impurity C (Aprepitant) | NMT 5% | 0.17 | 0.53 | 0.59 |
| Maximum unspecified impurity | NMT 0.2% | 0.04 | 0.04 | 0.04 |
| Total Impurities | NMT 6% | 0.12 | 0.63 | 0.65 |

Table 3 below includes accelerated stability testing data for the composition of Example 1, when stored at 25° C., 40% relative humidity.

TABLE 3

| | Specification | Initial | 2 M | 3 M |
|---|---|---|---|---|
| Description | CCS | CCS | CCS | CCS |
| pH | 6.5-10.0 | 8.68 | 8.87 | 8.68 |
| Assay of Fosaprepitant | 90-110% | 98.9 | 102.8 | 97.1 |
| Related Substances | | | | |
| Impurity C (Aprepitant) | NMT 5% | 0.17 | 0.73 | 1.24 |
| Maximum unspecified impurity | NMT 0.2% | 0.04 | 0.03 | 0.01 |
| Total Impurities | NMT 6% | 0.12 | 0.81 | 1.26 |

CCS: Clear colorless solution

Example 3

A fosaprepitant ready-to-use solution for infusion was prepared as detailed below.

| Ingredients | Quantity (mg/mL) | Quantity (% w/w) |
|---|---|---|
| Fosaprepitant Dimeglumine (equivalent to fosaprepitant) | 1.00 | 0.1 |
| Di sodium EDTA | 0.036 | 0.0036 |
| Lactose monohydrate | 2.50 | 0.25 |
| Polysorbate 80 | 0.50 | 0.05 |
| L-Arginine | 1.0 | 0.1 |
| Sodium Chloride | 8.00 | 0.8 |
| Streile Water for injection | Qs to 1 ml | |

80% of batch quantity of sterile water for injection was taken, and batch quantity of sodium chloride was added to the above solution under continuous stirring. Disodium EDTA was added with stirring. Lactose monohydrate was then added to the solution under stirring, followed by addition of L-Arginine and Polysorbate 80, and stirred until a clear homogenous solution was obtained. The fosaprepitant dimeglumine was then added to the solution under stirring and volume was made up to the batch size with water for injection. The solution was mixed until it was homogeneous, followed by cooling it to 5° C. The bulk solution thus obtained was filtered through 0.22 μm filter and filled into polypropylene infusion bags with twist off port.

Example 4

Three batches were made with a formula similar to that described in Example 3 above, and all three batches were subjected to stability testing under various conditions. The results of the stability testing are included in Tables 4 and 5 below.

TABLE 4

| | Batch 1 | | | | Batch 2 | | | | Batch 3 | | | |
|---|---|---|---|---|---|---|---|---|---|---|---|---|
| Condition | 2-8° C. | | | | 2-8° C. | | | | 2-8° C. | | | |
| Parameter | Initial | 1 M | 2 M | 3 M | Initial | 1 M | 2 M | 3 M | Initial | 1 M | 2 M | 3 M |
| Description | CCS | CCS | CCS | CCS | CCS | CCS | CCS | CCS | CCS | CCS | CCS | CCS |
| pH | 9.39 | 9.6 | 9.6 | 9.33 | 9.33 | 9.5 | 9.48 | 9.05 | 9.28 | 9.46 | 9.46 | 9.07 |
| Assay | 102.8 | 101.3 | 102.8 | 103.7 | 103.1 | 101.1 | 102.1 | 104.5 | 104 | 100.7 | 102.4 | 104 |
| Related Substances | | | | | | % w/w | | | | | | |
| Impurity-C (Aprepitant) | 0.23 | 0.41 | 0.52 | 0.48 | 0.28 | 0.4 | 0.5 | 0.49 | 0.29 | 0.43 | 0.52 | 0.47 |
| Impurity-F (%) | 0.02 | 0.01 | 0.08 | 0.05 | 0.02 | 0.01 | 0.08 | 0.06 | 0.02 | 0.01 | 0.07 | 0.04 |
| Maximum Unspecified Imp(%) | 0.04 | 0.03 | 0.03 | 0.04 | 0.04 | 0.03 | 0.03 | 0.03 | 0.04 | 0.03 | 0.03 | 0.04 |
| Total Impurities(%) | 0.37 | 0.49 | 0.69 | 0.60 | 0.39 | 0.48 | 0.68 | 0.62 | 0.43 | 0.51 | 0.68 | 0.59 |

ND: not detected

TABLE 5

| | Batch 1 | | | | Batch 2 | | | | Batch 3 | | | |
|---|---|---|---|---|---|---|---|---|---|---|---|---|
| Condition | 25 ± 2° C. | | | | 25 ± 2° C. | | | | 25 ± 2° C. | | | |
| Parameter | Initial | 1 M | 2 M | 3 M | Initial | 1 M | 2 M | 3 M | Initial | 1 M | 2 M | 3 M |
| Description | CCS | CCS | CCS | CCS | CCS | CCS | CCS | CCS | CCS | CCS | CCS | CCS |
| pH | 9.39 | 9.38 | 9.2 | 8.95 | 9.33 | 9.44 | 9.04 | 8.88 | 9.28 | 9.25 | 9.05 | 8.89 |
| Assay | 102.8 | 100.7 | 101.6 | 102.1 | 103.1 | 100.9 | 102.8 | 102.8 | 104 | 100.5 | 101.3 | 102.7 |
| Related impurities | | | | | | % w/w | | | | | | |

TABLE 5-continued

| | Batch No | | | | | | | | | | | |
|---|---|---|---|---|---|---|---|---|---|---|---|---|
| | Batch 1 | | | | Batch 2 | | | | Batch 3 | | | |
| | Condition | | | | | | | | | | | |
| | 25 ± 2° C. | | | | 25 ± 2° C. | | | | 25 ± 2° C. | | | |
| Parameter | Initial | 1 M | 2 M | 3 M | Initial | 1 M | 2 M | 3 M | Initial | 1 M | 2 M | 3 M |
| Impurity-C (Aprepitant) | 0.23 | 0.98 | 1.51 | 1.95 | 0.28 | 1.01 | 1.68 | 2.18 | 0.29 | 1.06 | 1.67 | 2.16 |
| Impurity-F (%) | 0.02 | 0.11 | 0.41 | 0.71 | 0.02 | 0.10 | 0.3 | 0.48 | 0.02 | 0.1 | 0.38 | 0.54 |
| Maximum Unspecified Imp(%) | 0.04 | 0.02 | ND | 0.03 | 0.04 | 0.02 | ND | 0.02 | 0.04 | 0.02 | ND | 0.02 |
| Total Impurities(%) | 0.37 | 1.20 | 1.92 | 2.71 | 0.39 | 1.21 | 1.98 | 2.64 | 0.43 | 1.27 | 2.05 | 2.74 |

Example 5

A fosaprepitant ready-to-use solution for infusion was prepared as detailed below.

| Ingredients | Quantity (% w/w) | Quantity Per bag (150 mL) |
|---|---|---|
| Fosaprepitant Dimeglumine | 0.1 | 150 mg |
| Di sodium EDTA | 0.0036 | 5.4 mg |
| Lactose monohydrate | 0.25 | 375 mg |
| L-Arginine | 0.1 | 150 mg |
| Sodium Chloride | 0.8 | 1200 mg |
| Polysorbate - 80 | 0.05 | 75 mg |
| Sterile water for injection | | QS to 150 mL |
| Nitrogen | | QS |

Qs: Quantity Sufficient

80% of batch quantity of sterile water for injection was taken, and batch quantity of sodium chloride was added to the above solution under continuous stirring.

Batch quantity of disodium edetate was then added to the above solution under continuous stirring to get clear solution. This was followed by addition of batch quantity of Lactose monohydrate under stirring. L-arginine was added with stirring. Polysorbate 80 was then added to the solution under stirring, followed by addition of fosaprepitant. The pH of the solution so obtained was found to be around pH 9.39. The volume of the solution was made up to 150 mL with sterile water for injection. The final pH of the solution was 9.39. This bulk solution was filtered under pressure using PVDF 0.22 μm membrane filter. 150 ml of the filtered solution was aseptically filled into nitrogen purged infusion bags made of polypropylene, free of any plasticizer and stored at 2-8° C.

Example 6

Three batches (5a, 5b and 5c) were made with a formula similar to that described in Example 5 above, and all three batches were subjected to stability testing under various conditions. The results of the stability testing are included in Tables 6.1, 6.2 and 6.3 and in Tables 7.1, 7.2 and 7.3 below.

TABLE 6.1

| | Batch# 5a | | | | | |
|---|---|---|---|---|---|---|
| Name of Test | | 5 ± 3° C. (Horizontal) | | | | |
| Parameter | Specification | Initial | 1 M | 2 M | 3 M | 6 M |
| Description | CCS | CCS | CCS | CCS | CCS | CCS |
| pH | 8.00-10.0 | 9.39 | 9.6 | 9.6 | 9.33 | 9.11 |
| Osmolality (mOsmol/kg) | 270-330 | 293 | 301 | 300 | 297 | 274 |
| Assay (%) | NLT 90% and NMT 110% | 102.8 | 101.3 | 102.8 | 103.7 | 101.5 |
| Related substances (% w/w) | | | | | | |
| Impurity-C (Aprepitant) | NMT 5.0% | 0.23 | 0.41 | 0.52 | 0.48 | 0.71 |
| Impurity-F | NMT 0.20% | 0.02 | 0.01 | 0.08 | 0.05 | 0.1 |
| Max. unspecified Impurity (%) | NMT 0.20% | 0.04 | 0.03 | 0.03 | 0.04 | 0.02 |
| Total Imp (%) | NMT 6.0% | 0.37 | 0.49 | 0.69 | 0.6 | 0.85 |

CCS: Clear colourless solution

TABLE 6.2

| | Batch# 5b | | | | | |
|---|---|---|---|---|---|---|
| Name of Test | | 5 ± 3° C. (Horizontal) | | | | |
| Parameter | Specification | Initial | 1 M | 2 M | 3 M | 6 M |
| Description | CCS | CCS | CCS | CCS | CCS | CCS |
| pH | 8.00-10.0 | 9.33 | 9.5 | 9.48 | 9.05 | 8.59 |

TABLE 6.2-continued

| | Batch# 5b | | | | | |
|---|---|---|---|---|---|---|
| Name of Test | | 5 ± 3° C. (Horizontal) | | | | |
| Parameter | Specification | Initial | 1 M | 2 M | 3 M | 6 M |
| Osmolality (mOsmol/kg) | 270-330 | 285 | NP | 280 | 306 | 265 |
| Assay (%) | NLT 90% and NMT 110% | 103.1 | 101.1 | 102.1 | 104.5 | 102.9 |
| Related substances (% w/w) | | | | | | |
| Impurity-C (Aprepitant) | NMT 5.0% | 0.28 | 0.40 | 0.50 | 0.49 | 0.71 |
| Impurity-F | NMT 0.20% | 0.02 | 0.01 | 0.08 | 0.06 | 0.08 |
| Max. unspecified Impurity (%) | NMT 0.20% | 0.04 | 0.03 | 0.03 | 0.03 | 0.02 |
| Total Imp (%) | NMT 6.0% | 0.39 | 0.48 | 0.68 | 0.62 | 0.82 |

CCS: Clear colourless solution

TABLE 6.3

| | Batch# 5c | | | | | |
|---|---|---|---|---|---|---|
| Name of Test | | 5 ± 3° C. (Horizontal) | | | | |
| Parameter | Specification | Initial | 1 M | 2 M | 3 M | 6 M |
| Description | CCS | CCS | CCS | CCS | CCS | CCS |
| pH | 8.00-10.0 | 9.28 | 9.46 | 9.46 | 9.07 | 8.81 |
| Osmolality (mOsmol/kg) | 270-330 | 287 | 278 | 284 | 278 | 263 |
| Assay (%) | NLT 90% and NMT 110% | 104 | 100.7 | 102.4 | 104 | 101.6 |
| Related substances (% w/w) | | | | | | |
| Impurity-C (Aprepitant) | NMT 5.0% | 0.29 | 0.43 | 0.52 | 0.47 | 0.8 |
| Impurity-F | NMT 0.20% | 0.02 | 0.01 | 0.07 | 0.04 | 0.09 |
| Max. unspecified Impurity (%) | NMT 0.20% | 0.04 | 0.03 | 0.03 | 0.04 | 0.03 |
| Total Imp (%) | NMT 6.0% | 0.43 | 0.51 | 0.68 | 0.59 | 0.92 |

CCS: Clear colourless solution

Tables 7.1, 7.2 and 7.3 below include accelerated stability testing data for the compositions of Example 5, when stored at 25° C., 60% relative humidity—

TABLE 7.1

| | Batch# 5a | | | | | |
|---|---|---|---|---|---|---|
| Name of Test | | 25 ± 2° C./60 ± 5% RH (Horizontal) | | | | |
| Parameter | Specification | Initial | 1 M | 2 M | 3 M | 6 M |
| Description | CCS | CCS | CCS | CCS | CCS | CCS |
| pH | 8.00-10.0 | 9.39 | 9.38 | 9.2 | 8.95 | 8.54 |
| Osmolality (mOsmol/kg) | 270-330 | 293 | 301 | NP | 302 | 303 |
| Assay (%) | NLT 90% and NMT 110% | 102.8 | 100.7 | 101.6 | 102.1 | 98.3 |
| Related substances (% w/w) | | | | | | |
| Impurity-C (Aprepitant) | NMT 5.0% | 0.23 | 0.98 | 1.51 | 1.95 | 2.77 |
| Impurity-F | NMT 0.20% | 0.02 | 0.11 | 0.41 | 0.71 | 1.12 |
| Max. unspecified Impurity (%) | NMT 0.20% | 0.04 | 0.02 | ND | 0.03 | 0.15 |
| Total Imp (%) | NMT 6.0% | 0.37 | 1.20 | 1.92 | 2.71 | 4.25 |

CCS: Clear colourless solution

TABLE 7.2

| | Batch# 5a | | | | | |
|---|---|---|---|---|---|---|
| Name of Test | 25 ± 2° C./60 ± 5% RH (Horizontal) | | | | | |
| Parameter | Specification | Initial | 1 M | 2 M | 3 M | 6 M |
| Description | CCS | CCS | CCS | CCS | CCS | CCS |
| pH | 8.00-10.0 | 9.33 | 9.44 | 9.04 | 8.88 | 8.4 |
| Osmolality (mOsmol/kg) | 270-330 | 285 | 284 | 282 | 283 | 288 |
| Assay (%) | NLT 90% and NMT 110% | 103.1 | 100.9 | 102.8 | 102.8 | 99.6 |
| Related substances (% w/w) | | | | | | |
| Impurity-C (Aprepitant) | NMT 5.0% | 0.28 | 1.01 | 1.68 | 2.18 | 3.63 |
| Impurity-F | NMT 0.20% | 0.02 | 0.10 | 0.3 | 0.48 | 0.75 |
| Max. unspecified Impurity (%) | NMT 0.20% | 0.04 | 0.02 | ND | 0.02 | 0.17 |
| Total Imp (%) | NMT 6.0% | 0.39 | 1.21 | 1.98 | 2.64 | 4.69 |

CCS: Clear colourless solution

TABLE 7.3

| | Batch# 5a | | | | | |
|---|---|---|---|---|---|---|
| Name of Test | 25 ± 2° C./60 ± 5% RH (Horizontal) | | | | | |
| Parameter | Specification | Initial | 1 M | 2 M | 3 M | 6 M |
| Description | CCS | CCS | CCS | CCS | CCS | CCS |
| pH | 8.00-10.0 | 9.28 | 9.25 | 9.05 | 8.89 | 8.46 |
| Osmolality (mOsmol/kg) | 270-330 | 287 | 274 | 281 | 283 | 286 |
| Assay (%) | NLT 90% and NMT 110% | 104 | 100.5 | 101.3 | 102.7 | 99.0 |
| Related substances (% w/w) | | | | | | |
| Impurity-C (Aprepitant) | NMT 5.0% | 0.29 | 1.06 | 1.67 | 2.16 | 2.76 |
| Impurity-F | NMT 0.20% | 0.02 | 0.1 | 0.38 | 0.54 | 0.81 |
| Max. unspecified Impurity (%) | NMT 0.20% | 0.04 | 0.02 | ND | 0.02 | 0.17 |
| Total Imp (%) | NMT 6.0% | 0.43 | 1.27 | 2.05 | 2.75 | 3.9 |

CCS: Clear colourless solution

The invention claimed is:

1. A stable ready-to-use pharmaceutical composition comprising: a) about 1 mg/mL of fosaprepitant or its pharmaceutically acceptable salt; b) at least one pharmaceutically acceptable solvent; c) at least one pharmaceutically acceptable isotonic agent so as to provide osmolarity of about 280 mOsMol/kg to about 320 mOsMol/kg; d) at least one pharmaceutically acceptable solubilizing agent and e) at least one pharmaceutically acceptable stabilizing agent, wherein the composition, when stored at about 2° C. to about 8° C. has at the end of its shelf-life:
(i) not more than 6% by total weight of the composition of total impurities,
(ii) not more than 0.2% by total weight of the composition of any unspecified impurity,
(iii) not more than 5% by total weight of the composition of impurity C (aprepitant),
(iv) not more than 0.2% by total weight of the composition of (3-(((2R,3S)-2-((S)-1-{3,5-bis(trifluoromethyl) phenyl) ethoxy)-3-(4-chlorophenyl)morpholino) methyl)-5-oxo-2,5-dihydro-1H-1,2,4-triazol-1-yl) phosphoric acid (impurity F);
and wherein the composition has a pH of about 6.5 to about 10.0.

2. The stable ready-to-use pharmaceutical composition of claim 1, wherein the pharmaceutically acceptable solvent is selected from the group consisting of water for injection, propylene glycol, polyethylene glycol, propanol and mixtures thereof.

3. The stable ready-to-use pharmaceutical composition of claim 1, wherein the solubilizing agent is a surfactant.

4. The stable ready-to-use pharmaceutical composition of claim 3, wherein the surfactant selected from docusate sodium, glyceryl monooleate, sodium lauryl sulfate, polysorbate 80 (polyoxyethylene sorbitan monooleate), polysorbate 40, polysorbate 20, polyoxyl-35-castor oil and mixtures thereof.

5. The stable ready-to-use pharmaceutical composition of claim 1, wherein the stabilizing agent is selected from the group consisting of (i) a chelating agent selected from the group consisting of disodium EDTA and calcium disodium EDTA, (ii) an amino acid selected from the group consisting of glycine, l-arginine, phenylalanine, histidine, acetylcysteine, citrulline, lysine, isoleucine, methionine, cysteine and their pharmaceutically acceptable salts, and (iii) a combination of chelating agent and amino acid.

6. The stable ready-to-use pharmaceutical composition of claim 1, wherein the isotonic agent is selected from polyethylene glycol, glycerol, sodium chloride, glucose and mixtures thereof.

7. The stable ready-to-use pharmaceutical composition of claim 1 comprising about 1 mg/ml of fosaprepitant, about 0.036 mg/ml of disodium EDTA, about 8 mg/ml of sodium chloride, about 2.5 mg/ml of lactose monohydrate, about 1 mg/ml of arginine, about 0.5 mg/ml of polysorbate 80 and sterile water for injection, wherein the composition has a pH of about 6.5 to about 10.0.

8. The stable ready-to-use pharmaceutical composition of claim 1, wherein the composition has a shelf-life of 24 months.

\* \* \* \* \*